United States Patent [19]

Sims et al.

[11] Patent Number: 5,288,507
[45] Date of Patent: Feb. 22, 1994

[54] IBUPROFEN ANTACID COMBINATIONS

[75] Inventors: Robert T. Sims, Holicong; Thomas N. Gates, Doylestown; William Slivka, Philadelphia, all of Pa.

[73] Assignees: Merck & Co., Inc., Rahway, N.J.; McNeill-PPC, Inc., Fort Washington, Pa.

[21] Appl. No.: 921,879

[22] Filed: Jul. 29, 1992

[51] Int. Cl.⁵ .................... A61K 33/06; A61K 33/08; A61K 33/10
[52] U.S. Cl. .................... 424/682; 424/683; 424/684; 424/685; 424/686; 424/687; 424/688; 424/689; 424/690; 424/691; 424/692; 514/557
[58] Field of Search ................. 514/557; 424/682–692

[56] References Cited

U.S. PATENT DOCUMENTS

| | | | |
|---|---|---|---|
| 4,279,926 | 7/1981 | Bruzzese et al. | 424/316 |
| 4,676,984 | 6/1987 | Wu et al. | 424/689 |
| 4,687,662 | 8/1987 | Schobel | 514/557 |
| 4,704,278 | 11/1987 | Wu et al. | 424/688 |
| 4,711,774 | 12/1987 | Denick et al. | 424/682 |
| 4,717,565 | 1/1988 | Denick | 424/683 |
| 4,761,274 | 8/1988 | Denick et al. | 424/684 |
| 4,831,058 | 5/1989 | Pankhania et al. | 514/557 |
| 4,851,444 | 7/1989 | Sunshine et al. | 514/570 |
| 4,857,324 | 8/1989 | Mir et al. | 424/690 |
| 4,873,231 | 10/1989 | Smith | 514/557 |
| 4,877,620 | 10/1989 | Loew et al. | 424/451 |
| 4,980,375 | 12/1990 | Sunshine et al. | 514/570 |
| 4,994,604 | 2/1991 | Tung et al. | 562/401 |
| 5,009,895 | 4/1991 | Lui | 424/465 |
| 5,034,416 | 7/1991 | Smith | 514/568 |

FOREIGN PATENT DOCUMENTS

| | | | |
|---|---|---|---|
| 0259990 | 3/1988 | European Pat. Off. | A61K 33/00 |
| 0377906 | 7/1990 | European Pat. Off. | A61K 9/46 |
| 0465235 | 1/1992 | European Pat. Off. | A61K 45/06 |
| 63-198620 | 8/1988 | Japan . | |
| 63-301817 | 12/1988 | Japan . | |

OTHER PUBLICATIONS

R. T. Schoen and R. J. Vender, Mechanisms of Nonsteroidal Antiinflammatory Drug-Induced Gastric Damage, Am. J. Med., 86, 449 (1989).
Physicians Desk Reference, p. 115 (1992).
The American Medical Association Guide to OTC and Prescription Drugs, p. 136 (1992).

Primary Examiner—Shep K. Rose
Attorney, Agent, or Firm—Melvin Winokur; David A. Muthard; Carol S. Quagliato

[57] ABSTRACT

This invention relates to a pharmaceutical composition for use in the treatment of pain and inflammation and the treatment of acid indigestion, sour stomach, heartburn and symptoms of upset stomach associated with these conditions in a mammalian organism, said composition comprising:

(i) an analgesically and anti-inflammatory effective amount of (S)-ibuprofen, or a salt thereof, substantially free of (R)-ibuprofen;
(ii) an amount effective in the treatment of acid indigestion, sour stomach and/or heartburn of at least one of the antacids; and
(iii) optionally, an amount effective in treating excess gas and flatulence of an anti-gas agent.

4 Claims, No Drawings

IBUPROFEN ANTACID COMBINATIONS

BACKGROUND OF THE INVENTION

The non-steroidal anti-inflammatory drugs (NSAID) have been utilized in the treatment of pain/inflammation and have been disclosed as useful in the treatment, management and mitigation of cold symptoms and the pain associated therewith.

Ibuprofen (2-(4-isobutylphenyl)propionic acid) is a well known and commonly employed NSAID. Recently, it has been found that a faster onset of pain relief and an enhanced analgesic response can be obtained by the utilization of the single enantiomer (S)-ibuprofen in comparison to racemic ibuprofen, (see for example U.S. Pat. No. 4,877,620).

Antacids are useful for the treatment of acid indigestion, heartburn, sour stomach, and symptoms of upset stomach associated with these conditions. Antacids work by neutralizing the excess stomach acid, thereby preventing inflammation, relieving pain, and allowing the mucous layer and lining to mend. In optional combination with an anti-gas agent, such as simethicone, antacids may offer relief or reduction of flatuence. Anti-gas remedies have a defoaming action that relieves or reduces flatulence by dispersing and preventing the formation of mucous-surrounded gas pockets in the gastrointestinal tract. Additionally, products which are combined with alginates float on the contents of the stomach and produce a neutralizing layer to subdue acid that can rise into the esophagus, causing heartburn.

Combinations of ibuprofen with antacid have not been disclosed, however, despite the fact that the acid indigestion, heartburn, sour stomach and upset stomach symptom sufferer is in need of quick and enhanced relief. Further, there has been no consideration has been given to the employment of (S)-ibuprofen, and more particularly a lysine or arginine salt thereof, in combination with an antacid for the treatment of acid indigestion, heartburn, sour stomach and symptoms of upset stomach associated with these conditions.

DETAILED DESCRIPTION OF THE INVENTION

This invention relates to a pharmaceutical composition for use in the treatment of pain and inflammation and the treatment of acid indigestion, heartburn, sour stomach and symptoms of upset stomach associated with these conditions, in a mammalian organism, said composition comprising:
(i) an analgesically and anti-inflammatory effective amount of (S)-ibuprofen, or a salt thereof, substantially free of (R)-ibuprofen; and
(ii) an amount effective in the treatment of acid indigestion, heartburn, sour stomach and symptoms of upset stomach associated with these conditions of at least one of the antacids.

This invention is also directed to a method of treating pain and inflammation and the treatment of acid indigestion, heartburn, sour stomach and symptoms of upset stomach associated with these conditions in a mammalian organism in need of such treatment, comprising administering to such organism:
(i) an analgesically and anti-inflammatory effective amount of (S)-ibuprofen, or a salt thereof, substantially free of (R)-ibuprofen; and
(ii) an amount effective in the treatment of acid indigestion, heartburn, sour stomach and symptoms of upset stomach associated with these conditions of at least one of the antacids.

This invention is also directed to a method of eliciting an onset hastened and enhanced response for the treatment of pain and inflammation and the relief of gastrointestinal distress in a mammalian organism in need of such treatment, comprising administering to such organism:
(i) an analgesically and anti-inflammatory effective amount of (S)-ibuprofen, or a salt thereof, substantially free of (R)-ibuprofen; and
(ii) an amount effective in the treatment of acid indigestion, heartburn, sour stomach and symptoms of upset stomach associated with these conditions of at least one of the antacids.

Substantially free of (R)-ibuprofen should be taken to mean that the ratio of (S)-ibuprofen to (R)-ibuprofen is at least 90:10.

Salts of (S)-ibuprofen include salts with alkali metals, such as sodium or potassium, salts with alkaline earth metals, such as calcium, or salts with other metals such as magnesium, aluminum, iron, zinc, copper, nickel or cobalt.

Salts of (S)-ibuprofen further include the amino acid salts, particularly the basic amino acids such as lysine or arginine. Specifically included within the above composition is (S)-ibuprofen-(S)-lysine and (S)-ibuprofen-(R)-lysine.

(S)-ibuprofen may be prepared following the procedures disclosed in U.S. Pat. No. 4,877,620. Metal salts of ibuprofen may be obtained by contacting a hydroxide, or carbonate with ibuprofen. Amino acid salts of ibuprofen may be obtained by contacting an amino acid in solution with ibuprofen.

The pharmaceutical compositions of the present invention are useful in the treatment of pain and inflammation and acid indigestion, sour stomach, heartburn, flatulence (when an optional anti-gas agent is included in the composition) and symptoms of upset stomach associated with these conditions.

The utilization of (S)-ibuprofen in an analgesic/antacid combination composition offers significant advantages over the combination of racemic ibuprofen with an analgesic. (S)-Ibuprofen provides a faster onset of pain relief and an enhanced degree of relief compared to racemic ibuprofen. These benefits are increased in an (S)-ibuprofen/antacid combination as the antacid potentiates the action of (S)-ibuprofen. This has not heretofore been observed because the art has not proposed the combination of the (S)-ibuprofen enantiomer, absent (R)-ibuprofen, with an antacid. The presence of the (R)-ibuprofen may blur the potentiated effect.

Furthermore, the absence of (R)-ibuprofen provides significant benefits particularly to the organism in a weakened state due to upset stomach symptoms. The allergic contraindications sometimes associated with ibuprofen administration, and which may be particularly detrimental to the upset stomach sufferer, are absent or reduced in a composition wherein the (R)-ibuprofen is absent. Furthermore, the organism using the (S)-ibuprofen/antacid combination will no longer need to divert metabolic energy to the inversion of the (R)-enantiomer or the removal of this enantiomer. The absence of inversion reduces or eliminates the formation and incorporation into fatty tissue of hybrid-ibuprofen containing triglycerides. The absence of the (R)-ibuprofen in an (S)-ibuprofen/antacid combination is also particularly advantageous as a lesser metabolic burden is placed on the urogenital system for the excretion of the (R)-entantiomer or its metabolites. The renal burden and renal toxicities sometimes associated with ibuprofen therapy are reduced or absent in a substantially (R)-ibuprofen free composition.

The absence of the inactive enantiomers, (R)-ibuprofen, provides for significant size and weight advantages in a combination dosage form, particularly a sustained release dosage form. Where a sustained release dosage of ibuprofen may have required 800 to 1000 mg, the employment of (S)-ibuprofen reduces the weight to 400 to 500 mg, and provides for a more practical size tablet for an ibuprofen/antacid combination.

An effective amount of (S)-ibuprofen, or a pharmaceutically acceptable salt thereof, for use in an unit dose composition of this invention may range from 50 to 800 mg (S)-ibuprofen. The preferred amount of (S)-ibuprofen is about 100 to 400 mg. The amount of a salt such as (S)-ibuprofen-(S)-lysine is determined based on the amount of (S)-ibuprofen contained therein.

(S)-ibuprofen may be prepared following the procedures disclosed in U.S. Pat. No. 4,877,620. Metal salts of ibuprofen may be obtained by contacting a hydroxide, or carbonate with ibuprofen. Amino acid salts of ibuprofen may be obtained by contacting an amino acid in solution with ibuprofen. U.S. Pat. No. 4,994,604 describes a process for the formation and resolution of (S)-ibuprofen-(S)-lysine that employs preferential crystallization to separate a pair of diastereomeric salts, (S)-ibuprofen-(S)-lysine and (R)-ibuprofen-(S)-lysine. The basic procedure involves (a) contacting (R),(S)-ibuprofen and (S)-lysine in an aqueous-organic solvent mixture; (b) separating any suspended solid from the mixture; and (c) cooling the clear mixture until the mixture is supersaturated with respect to each of the (S)-ibuprofen-(S)-lysine and (R)-ibuprofen-(S)-lysine salts; (d) contacting the supersaturated mixture with a slurry of (S)-ibuprofen-(S)-lysine in an aqueous-organic solvent; and (e) separating the formed crystalline (S)-ibuprofen-(S)-lysine.

Specifically, the racemic ibuprofen starting material is mixed with an organic solvent that is miscible with water. The (S)-lysine is mixed with water and the ibuprofen and lysine solutions are combined. The mixture is agitated for a time period sufficient to crystallize all the salts, if any, in excess of the solubility limit. The suspended salts are separated to obtain a clear mother liquor which is generally saturated with respect to the diastereomeric salts (S)-ibuprofen-(S)-lysine and (R)-ibuprofen-(S)-lysine. Filtration may be employed to effect the separation. The liquor is then cooled to a temperature at which it is supersaturated with respect to each of the diastereomeric salts. It is preferred that the liquor be cooled to the point at which maximum supersaturation is obtained with respect to each salt without nucleation of either crystallizable species. Typically the temperature of the mother liquor must be lowered by about 5° C. to reach maximum supersaturation without precipitation of either salt. However, the degree of cooling will depend on the particular solvent composition. The supersaturated liquor is then passed into a vessel containing a slurry of (S)-ibuprofen-(S)-lysine, hereafter referred to as the (S,S) salt, in the same solvent system employed above for the mixture of racemic ibuprofen and (S)-lysine. In the presence of the (S,S) salt crystals acting as a seed, the supersaturation of the (S,S)-salt in the feed liquor is released by the growth of further crystals of the (S,S)-salt. Conversely, there is little or no change in the (R)-ibuprofen-(S)-lysine supersaturation because the growth rate of the (R,S) crystals is essentially zero in the absence of any initial (R,S) salt seed. The (S,S) crystals are then separated by filtration or centrifugation, and washed with aqueous-organic solvent to yield (S)-ibuprofen-(S)-lysine of purity approximating 98%.

The antacid employed herein is of the conventional type typically found in over the counter therapies for the relief of acid indigestion, sour stomach, heartburn and symptoms of upset stomach associated with these conditions. The antacid usually works by neutralizing excess stomach acid, thereby reducing or preventing inflammation, relieving pain and allowing the mucous layer and lining to mend. The term "antacid" includes but is not limited to: aluminum hydroxide, aluminum hydroxide with magnesium carbonate, calcium carbonate, magnesium hydroxide, magnesium oxide and magnesium trisillicate. In addition a second antacid ingredient may be employed. Such a second antacid includes those antacids described above and, in addition, magnesium carbonate, magaldrate and dihydroxy aluminum sodium carbonate.

The amount of the antacid useful in the practice of the present invention may vary from about 5 mg to 1500 mg depending on the specific antacid. When the composition is administered in the form of a tablet or capsule, the amount of antacid may vary from about 20 to 1500 mg per tablet/capsule. When the composition is administered in the form of an elixir, syrup or suspension the amount of antacid may vary from about 5 mg to 150 mg per mL of composition.

A preferred embodiment of the composition of the instant invention in the form of a tablet or capsule comprises aluminum hydroxide in the amount of from about 200-400 mg, magnesium hydroxide in the amount of from 200 to 400 mg and simethicone in the amount in the amount of from 0 to 40 mg. A preferred embodiment of the composition of the instant invention has the aluminum hydroxide and the magnesium hydroxide in a ratio of 1:1. A preferred embodiment of the composition of the instant invention in the form of an elixir, syrup or suspension comprises (per mL of liquid) aluminum hydroxide in the amount of from about 40 to 80 mg, and simethicone in the amount of from about 4 to 8 mg.

In addition to the analgesic and antacid, the composition of the instant invention may further comprise an antifoaming agent which can act to relieve symptoms, associated with excess gas including flatulence, which may often accompany gastrointestinal disturbance. Such an anti-foaming agent is selected from simethicone and the like.

On the other hand, in addition to the analgesic and antacid there may be included in the composition of the instant invention a foaming agent, which can act to create a foam which can act as a physical barrier which blocks stomach acids from backing up into the esophagus thereby causing heartburn. Such a foaming agent is selected from sodium alginate and the like.

The composition of the instant invention may further comprise an antiulcerative agent such as sucralfate, misoprostol and the like. The composition of the instant invention may also further comprise an pro-motility agent to improve gastro/esophageal peristalsis and relieve the symptoms of indigestion. Such an pro-motility agent is selected from metoclopramide hydrochloride, cisapride and the like.

The instant composition may be administered in the form of tablets, caplets, gelcaps, capsules, elixirs, syrups or a suspension. For oral administration the active components may be admixed with a pharmaceutically acceptable diluent such as lactose, starch, sucrose, cellulose, magnesium stearate, dicalcium phosphate, calcium sulfate, mannitol, sodium bicarbonate, potassium bicarbonate, citric acid, glycine, sodium citrate, pectin, sodium tartrate, alginic acid, calcium stearate, bismuth subnitrate, bismuth subgallate, bismuth subcarbonate, bismuth subsalicylate, hydroxypropyl methylcellulose, and in a liquid composition, ethyl alcohol. Acceptable binders such as PVP, starch, gelatin, natural sugars, corn sweeteners, natural and synthetic gums such as acacia, sodium alginate, carboxymethylcellulose, polyethylene glycol and waxes, may also be admixed with the active components. Where necessary lubricants such as magnesium stearic acid talc, and disintegrators such as starch, methylcellulose, agar, bentonite and guar gum and super disintegrators such as docusate sodium, sodium starch glycollate or cross linked PVP may also be included.

The active components may also be formulated in sustained release formulations. These formulations may be employed in oral, dermal, rectal or vaginal administrations. Such sustained release forms also include layered formulations which provide for distinct release ratio and thus may be more beneficial in allowing for short and long term relief.

The following examples illustrate the compositions of the present invention and as such are not to be considered as limiting the invention set forth in the claims appended hereto.

EXAMPLE 1
(S)-Ibuprofen, Antacid Tablet

| | |
|---|---|
| (S)-ibuprofen-(S)-lysine | 342 mg |
| Aluminum Hydroxide | 250 mg |
| Magnesium Hydroxide | 250 mg |
| PVP | 15 mg |
| Avicel PH101 | 40 mg |
| Magnesium Stearate | 4 mg |

EXAMPLE 2
(S)-Ibuprofen, Antacid, Anti-Gas Tablet

| | |
|---|---|
| (S)-ibuprofen-(S)-lysine | 342 mg |
| Aluminum Hydroxide | 250 mg |
| Magnesium Hydroxide | 250 mg |
| PVP | 15 mg |
| Avicel PH101 | 40 mg |
| Magnesium Stearate | 4 mg |
| Simethicone | 30 mg |

EXAMPLE 3
(S)-ibuprofen, Antacid Sustained Release

| | |
|---|---|
| (S)-ibuprofen | 400 mg |
| Aluminum Hydroxide | 250 mg |
| Magnesium Hydroxide | 250 ml |
| PVP | 30 mg |
| Avicel PH101 | 80 mg |
| Magnesium Stearate | 8 mg |
| Methocel E10MCR | 66 mg |
| Methocel K100MLV | 200 mg |

EXAMPLE 4
(S)-ibuprofen, Antacid, Anti-Gas Sustained Release

| | |
|---|---|
| (S)-ibuprofen | 400 mg |
| Aluminum Hydroxide | 250 mg |
| Magnesium Hydroxide | 250 ml |
| PVP | 30 mg |
| Avicel PH101 | 80 mg |
| Magnesium Stearate | 9 mg |
| Methocel E10MCR | 66 mg |
| Methocel K100MLV | 200 mg |
| Simethicone | 30 mg |

EXAMPLE 5
(S)-ibuprofen-(s)-lysine/Antacid Solution

| | |
|---|---|
| (S)-ibuprofen-(S)-lysine | 342 mg |
| Aluminum Hydroxide | 300 mg |
| g.s. syrup | 5 ml |

EXAMPLE 6
(S)-ibuprofen-(s)-lysine/Antacid, Anti-Gas Solution

| | |
|---|---|
| (S)-ibuprofen-(S)-lysine | 342 mg |
| Aluminum Hydroxide | 250 mg |
| Magnesium Hydroxide | 250 mg |
| g.s. syrup | 5 ml |
| Simethicone | 30 mg |

EXAMPLE 7
(S)-ibuprofen-(s)-lysine/Antacid, Anti-Gas Solution

| | |
|---|---|
| (S)-ibuprofen-(S)-lysine | 342 mg |
| Aluminum Hydroxide | 200 mg |
| Magnesium Hydroxide | 200 mg |
| g.s. syrup | 5 ml |
| Simethicone | 30 mg |

EXAMPLE 8
(S)-ibuprofen-(s)-lysine/Antacid, Anti-Gas Solution

| | |
|---|---|
| (S)-ibuprofen-(S)-lysine | 342 mg |
| Aluminum Hydroxide | 400 mg |
| Magnesium Hydroxide | 400 mg |
| g.s. syrup | 5 ml |
| Simethicone | 30 mg |

What is claimed is:

1. A method of treating of pain and inflammation and the treatment of acid indigestion, heartburn, sour stomach, and symptoms of upset stomach associated with these conditions in a mammalian organism in need of such treatment, comprising administering to such organism:
   (i) an analgesically and anti-inflammatory effective amount of a salt of (S)-ibuprofen, substantially free of (R)-ibuprofen wherein the salt is selected from (S)-ibuprofen-(S)-lysine and (S)-ibuprofen-(R)-lysine; and
   (ii) an amount effective in the treatment of acid indigestion, heartburn, sour stomach, and symptoms of upset stomach associated with these conditions of aluminum hydroxide with magnesium hydroxide.

2. A method of eliciting an onset hastened and enhanced response for the treatment of pain and inflammation and the treatment of acid indigestion, heartburn, sour stomach, and symptoms of upset stomach associated with these conditions in a mammalian organism in need of such treatment, comprising administering to such organism:
   (i) an analgesically and anti-inflammatory effective amount of a salt of (S)-ibuprofen, substantially free of (R)-ibuprofen wherein the salt is selected from (S)-ibuprofen-(S)-lysine and (S)-ibuprofen-(R)-lysine; and
   (ii) an amount effective in the treatment of acid indigestion, heartburn, sour stomach, and symptoms of upset stomach associated with these conditions of aluminum hydroxide with magnesium hydroxide.

3. A method of reducing the side effects associated with the administration of an ibuprofen/antacid combination which comprises the administration of a salt of (S)-ibuprofen, substantially free of (R)-ibuprofen wherein the salt is selected from (S)-ibuprofen-(S)-lysine and (S)-ibuprofen-(R)-lysine, and aluminum hydroxide with magnesium hydroxide.

4. A method of reducing the size and weight of an ibuprofen/antacid combination dosage form which comprises combining a salt of (S)-ibuprofen, substantially free of (R)-ibuprofen wherein the salt is selected from (S)-ibuprofen-(S)-lysine and (S)-ibuprofen-(R)-lysine, and aluminum hydroxide with magnesium hydroxide.

* * * * *